United States Patent [19]

Brown

[11] Patent Number: 5,670,502

[45] Date of Patent: Sep. 23, 1997

[54] METHOD OF TUMOR TREATMENT

[75] Inventor: J. Martin Brown, Redwood City, Calif.

[73] Assignee: The Board of Trustees of Leland Stanford Jr. Univ., Stanford, Calif.

[21] Appl. No.: 448,705

[22] Filed: May 24, 1995

Related U.S. Application Data

[62] Division of Ser. No. 125,609, Sep. 22, 1993.

[51] Int. Cl.⁶ .................... A61K 31/53; A61K 31/535; A61K 31/675; A61K 31/28

[52] U.S. Cl. .................... 514/243; 514/81; 514/235.2; 514/234.2; 514/492

[58] Field of Search .................... 514/492, 243, 514/81, 235.2, 234.2

[56] References Cited

U.S. PATENT DOCUMENTS 5,175,287  12/1992  Lee et al. .................... 544/183

OTHER PUBLICATIONS

Zeman et al., JWT J. Radiation Oncology, Biol Phys., vol. 12, pp. 1239–1242 (1986).

The Merck Index, 11th ED., Merck +Co, Inc, Rahway, N.J., 1989, p. 1822.

*Primary Examiner*—Jerome D. Goldberg
*Attorney, Agent, or Firm*—William J. Davis; Imre Balogh

[57] ABSTRACT

The present invention provides methods for treating mammalian cancer tumors, preferably solid tumors, comprising administering to a mammal in need of such treatment an effective amount of a 1,2,4-benzotriazine oxide as defined in Formula I or pharmacologically acceptable salts of said compound; and administering to the mammal from about one half hour to about twenty-four hours after administering the 1,2,4-benzotriazine oxide an effective amount of a chemotherapy agent to which the minor is susceptible. The invention also provides kits for treatment of such tumors which comprise a chemotherapy agent and a cytotoxicity-enhancing amount of a 1,2,4-benzotriazine oxide as defined in Formula I.

12 Claims, 1 Drawing Sheet

METHOD OF TUMOR TREATMENT

This application is a division of application Ser. No. 08/125,609, filed on Sep. 22, 1993.

1. Field of the Invention

The present invention relates to the field of treatments for cancer tumors. More particularly the present invention relates to treatment of cancer tumors with combinations of chemotherapy agents and 1,2,4-benzotriazine oxides.

2. Background of the Invention

The most commonly used anticancer drugs are more ctyotoxic toward normally oxygenated tumor cells than toward hypoxic tumor cells. Hypoxic cell resistance to irradiation is also widely known. Consequently, minor hypoxia and the resultant resistance to treatment is of concern in cancer therapeutics.

Solid cancer tumors contain both adequately oxygenated cells as well as varying proportions of inadequately oxygenated or hypoxic cells. Hypoxia usually occurs where the tumor cells are furthest away from blood vessels. Such cells also tend to have slower rates of proliferation. Although not completely understood, resistance of hypoxic cells to anti-cancer drugs is generally thought to be due to inadequate uptake of the drug by the hypoxic cells either because they tend to be slowly growing or because of their distance from the blood vessels bringing the drug. Thus, the relative proportion of hypoxic cells in the tumor can be of great importance to the outcome of the treatment Resistant hypoxic cells that survive in irradiation or drug treatment may become reoxygenated, thereby restoring tumor sensitivity to further treatment. Nonetheless, instead of relying on uncertain events, it is desirable to develop cancer treatments wherein cancer tumor cells, including hypoxic tumor cells, are killed or rendered inactive more reliably at the time the treatment is administered.

U.S. Pat. No. 5,175,287 issued Dec. 29, 1992 discloses the use of 1,2,4-benzotriazine oxides in conjunction with radiation for treatment of tumors. The 1,2,4-benzotriazine oxides sensitize the tumor cells to radiation and make them more amenable to this treatment modality.

Holden et al. (1992) "Enhancement of Alkylating Agent Activity by SR-4233 in the FSaIIC Murine Fibrosarcoma" JNCI 84:187-193 discloses the use of SR-4233, also known as tirapazamine, in combination with an antitumor alkylating agent. The four antitumor alkylating agents, cisplatin, cyclophosphamide, carmustine and melphalan, were each tested to examine the ability of tirapazamine to overcome the resistance of hypoxic minor cells to antitumor alkylating agents. Tirapazamine was tested alone and in combination with varying amounts of each of the antitumor alkylating agents. When SR 4233 was administered just before single-dose treatment with cyclophosphamide, carmustine or melphalan marked dose enhancement leading to synergistic cytotoxic effects on tumor cells was observed. When SR 4233 was administered just prior to single-dose treatment with cisplatin, however, the dose enhancement lead to an additive effect, except at the highest dose level of cisplatin.

Nitroimidazole hypoxic cytotoxic agents have been combined with various anti-cancer drugs and it was found that a therapeutic gain could be achieved when these agents were combined with various anti-cancer drags, particularly the alkylating agents, cyclophosphamide and melphalan and the nitrosoureas, BCNU and CCNU. However, it was later found that the therapeutic gain produced was not the consequence of selective killing of hypoxic cells by the nitroimidazoles but appeared to be by a mechanism involving the potentiation of alkylating agent-induced DNA cross-links by metabolites of the nitroimidazoles (Murray et al. (1983) Br. J. Cancer 47: 195–203).

SUMMARY OF THE INVENTION

The present invention provides methods of treating cancer tumors, particularly solid minors comprising administering to a mammal in need of such treatment an effective amount of a compound having the formula

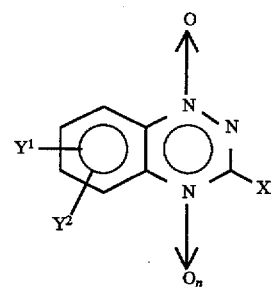

Formula I wherein X is H; hydrocarbyl (1–4C); hydrocarbyl (1–4C) substituted with OH, $NH_2$, NHR or NRR; halogen; OH; alkoxy (1–4C); $NH_2$; NHR or NRR; wherein the various R groups are independently selected from lower alkyl (1–4C) and lower acyl (1–4C) and the R's may themselves be substituted with OH, $NH_2$, alkyl (1–4C) secondary and dialkyl (1–4C) tertiary amino groups, alkoxy (1–4C) or halogen. In the case of NRR, the two R's can be linked together directly or through a bridge oxygen into a morpholino ting, pyrrolidino ring or piperidino ring;

n is 0or 1; and $Y^1$ and $Y^2$ are independently either H; nitro; halogen; hydrocarbyl (1–14C) including cyclic and unsaturated hydrocarbyl, optionally substituted with 1 or 2 substituents selected from the group consisting of halogen, hydroxy, epoxy, alkoxy (1–4C), alkylthio (1–4C), primary amino ($NH_2$), alkyl (1–4C) secondary amino, dialkyl (1–4C) tertiary amino, dialkyl (1–4C) tertiary amino where the two alkyls are linked together to produce a morpholino, pyrrolidino or piperidino, acyloxy (1–4C), acylamido (1–4C) and thio analogs thereof, acetylaminoalkyl (1–4C), carboxy, alkoxycarbonyl (1–4C), carbamyl, alkylcarbamyl (1–40, alkylsulfonyl (1–4C) or alkylphosphonyl (1–4C), wherein the hydrocarbyl can optionally be interrupted by a single ether (—O—) linkage; or wherein $Y^1$ and $Y^2$ are independently either morpholino, pyrrolidino, piperidino, $NH_2$, NHR', NR'R'O(CO)R', NH(CO)R', O(SO)R', or O(POR')R' in which R' is a hydrocarbyl (1–4C) which may be substituted with OH, $NH_2$, alkyl (1–4C) secondary amino, dialkyl (1–4C) tertiary amino, morpholino, pyrrolidino, piperidino, alkoxy (1–4C), or halogen substituents, or pharmacologically acceptable salts of said compound; and administering to the mammal from about one half hour to about twenty-four hours after administering the compound of Formula I, as defined herein, an effective amount of a chemotherapy agent to which the tumor is susceptible.

The present invention also provides methods of increasing the toxicity of chemotherapy agents towards solid tumors. In this aspect of the invention a cytotoxicity-enhancing amount of a compound of Formula I, as defined hereinabove, is administered to a mammal having a solid tumor and in need of such treatment, the tumor further being susceptible to treatment with the chemotherapy agent, about one half hour to about twenty-four hours prior to administering the chemotherapy agent, or about one hour to about two hours after administering the chemotherapy agent.

In another aspect, the present invention provides a method of treating mammalian cancer tumors comprising administering a compound of Formula I, as defined herein, to the mammal one to two hours after administration of a chemotherapy agent.

Applicants have discovered that administering a compound of Formula I, as defined herein, either before or after the administration of a chemotherapy agent surprisingly and unexpectedly killed tumor cells to a much greater extent than administration of either agent alone, or administration of both agents at the same time. When tirapazamine was administered up to twenty-four hours prior to administration of cisplatin, Applicants found there was a ten to one thousand fold increase in tumor cell killing above the amount of minor cell killing found when tirapazamine and cisplatin were administered at the same time. The greatest synergistic effect with this combination of gents was found when tirapazamine was administered about two and one half hours prior to administration of cisplatin.

Applicants' claimed method represents an enormous increase in anti-tumor efficacy of the chemotherapy agent (i.e. its cytotoxic effects upon tumor cells). Additionally, in tests of the systemic toxicity of cisplatin (serum BUN and acute toxicity) the combination with the optimum separation for tumor efficacy showed little or no enhancement of systemic toxicity compared to cisplatin alone. Thus, most, if not all, of the additional cell kill of the tumor cells translates into a therapeutic gain for this combination. The synergistic interaction between tirapazamine and cisplatin is also significant since the great increase in tumor cell killing was produced at a relatively low dose of cisplatin.

The present invention is more particularly pointed out in the appended claims and is described in its preferred embodiments in the following description.

Figure 1:
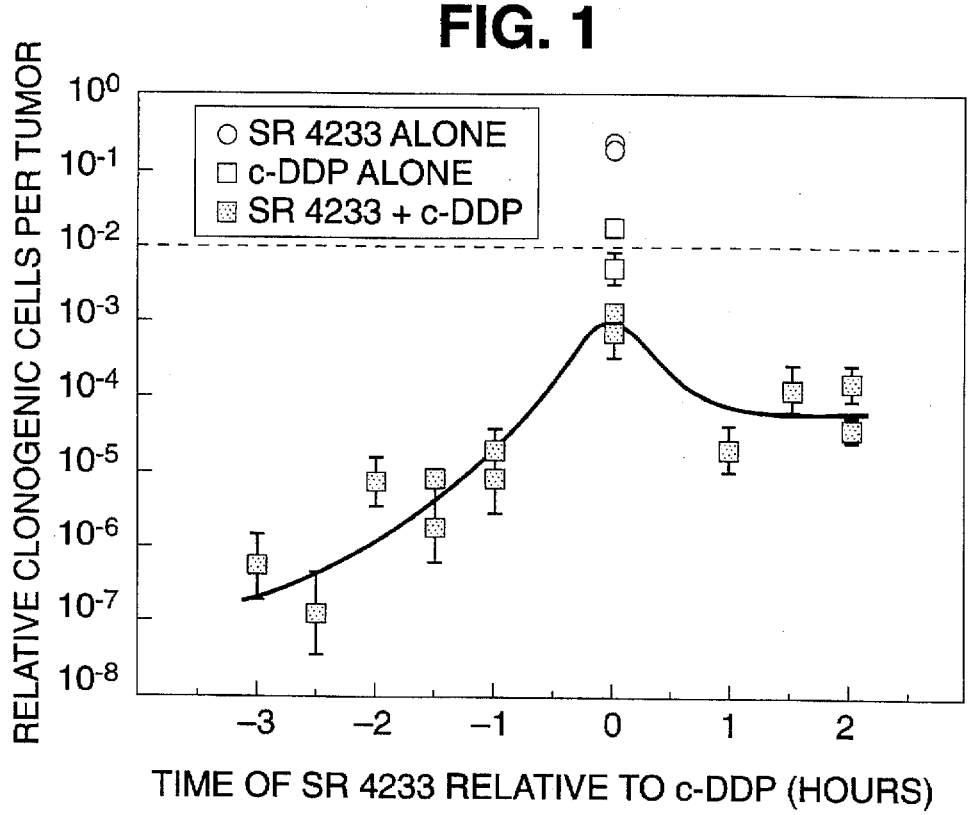
FIG. 1 shows a graph of the relative clonogenic cells per tumor present in experimental RIF-1 minors versus time (−3 to +2 hours) of administration of tirapazamine relative to cisplatin.

DETAILED DESCRIPTION OF THE INVENTION.

The present invention provides methods for treating mammalian cancer tumors, including human cancer tumors, particularly solid tumors. In this aspect of the invention, an effective amount of a compound having Formula I, as defined herein, is administered to a mammal having a cancer minor and in need of such treatment from about one half hour to about twenty-four hours before an effective amount of a chemotherapy agent to which the tumor is susceptible is administered to the mammal.

As used herein, susceptibility of a tumor to a chemotherapy agent refers to a chemotherapty agent that is capable of exerting a therapeutic effect on a tumor by any mechanism such as by killing tumor cells, reducing cell proliferation or reducing the size of the tumor. Also as used herein, effective mount of the compound of Formula I, as defined herein, refers to amounts capable of killing tumor cells or capable of killing tumor cells in conjunction with a chemotherapy agent. An effective amount of a chemotherapy agent refers to an amount of the chemotherapy agent capable of killing cancer cells or otherwise producing a therapeutic effect such as by reducing tumor size or slowing tumor cell growth and proliferation.

Another aspect of the invention provides a method for increasing the cytotoxicity of a chemotherapy agent towards a solid tumor susceptible to treatment with the chemotherapy agent comprising, administering a cytotoxicity-enhancing amount of a compound of Formula I, as defined herein, to a mammal having such a tumor from about one hour to about two hours after administering the chemotherapy agent. As used herein, the term cytotoxicity-enhancing amount refers to an amount of the compound of Formula I, as defined herein, that is capable of increasing the cytotoxic effects of the chemotherapy agent on cells. Preferably the cytotoxicity-enhancing mount is sufficient to produce a synergistic effect, i.e., greater than the sum of the effects of the chemotherapy agent and the compound of Formula I when administered singly. Cytotoxicity-enhancing mounts of the of the compound of Formula I can be assessed by testing such compounds with a chemotherapy agent(s) in in vivo and/or in vitro experimental tumor models, such as the one set forth herein, or any other tumor model known in the art. The cytotoxicity-enhancing amount determined through in vivo and or in vitro experimental tumor models is then used as a guide for determining the amounts of the two agents that will he administered to the mammal for treatment of the tumor.

Another further aspect of the invention provides methods for increasing the cytotoxicity of a chemotherapy agent towards a solid tumor susceptible to treatment with the chemotherapy agent, comprising administering to a mammal having such a tumor a cytotoxicity-enhancing amount of a compound having Formula I, as defined herein, from about one hour to about two hours after administering a chemotherapy agent Without wishing to be bound by any theory or mode of action, at the present time it is believed that the combination of a benzotriazine chemotherapy agent of Formula I, as defined herein, that is specifically cytotoxic to hypoxic cancer cells and a chemotherapy agent having its greatest activity on normally oxygenated cancer cells provides enhanced or synergistic killing of rumor cells. The benzotriazines oxides of Formula I, as defined herein, specifically require lower than normal oxygen concentrations in order to exert their effects. This requirement for hypoxia is a major advantage, since it provides the basis for rumor-specific interaction between the two drags. In general, normal tissues are at an oxygen concentration above 10–15 mm Hg. At these and higher oxygen partial pressures, the cytotoxicity produced by tirapazamine is very low. On the other hand, many tumors have a significant number of cells at oxygen concentrations below 10 mm Hg, at which partial pressures the metabolism of tirapazamine and the other benzotriazines of Formula I to cytotoxic species is greatly increased. As used herein hypoxic minor cells refers to tumor cells at an oxygen partial pressure less than about 10 mm Hg.

The methods of the present invention are useful in the treatment of mammalian cancer tumors, including human cancer minors, particularly solid minors having hypoxic regions. Examples of such minors include, but are not limited to, adrenocarcinomas, glioblastomas (and other brain minors), breast, cervical, colorectal, endometrial, gastric, liver, lung (small cell and non-small cell), lymphomas (including non-Hodgkin's, Burkitt's, diffuse large cell, follicular and diffuse Hodgkin's), melanoma (metastatic), neuroblastoma, osteogenic sarcoma, ovarian, retinoblastoma, soft tissue sarcomas, testicular and other tumors which respond to chemotherapy. Thus, the methods of the present invention can be used to treat cancer tumors, including experimentally-induced cancer tumors, in any type of mammal including humans, commonly used laboratory animals such as rats, mice, rabbits and dogs, primates such as monkeys, and horses, cats and other animals.

The methods of the present invention can be practiced with any type of chemotherapy agent. In any particular embodiment of the invention, the chemotherapy agent will be selected with reference to factors such as the type of cancer tumor and the efficacy of the chemotherapy agent for treating the cancer tumor involved. The chemotherapy agent may selected from alkylating agents, antimetabolites, natural products, hormones and antagonists and other types of compounds.

Examples of alkylating agents include the nitrogen mustards (i.e. the 2-chloroethylamines) such as, for example, chloromethine, chlorambucil, melphalan, uramustine, mannomustine, extramustine phosphate, mechlorthaminoxide, cyclophosphamide, ifosamide and trifosfamide; alkylating agents having a substituted aziridine group such as, for example, tretamine, thiotepa, triaziquone and mitomycin; alkylating agents of the alkyl sulfonate type, such as, for example, busulfan, and piposulfan; alkylating N-alkyl-N-nitrosourea derivatives such as, for example, carmustine, lomustine, semustine or streptozotocine; alkylating agents of the mitobronitole, dacarbazine and procarbazine type; and platinum complexes such as, for example, cisplatin and carboplatin.

Examples of antimetabolites include folic acid derivatives such as, for example, methotrexate, aminopterin and 3'-dichloromethotrexate; pyrimidine derivatives such as, for example, 5-fluorouracil, floxuridine, tegafur, cytarabine, idoxuridine, and flucytosine; purine derivatives such as, for example, mercaptopurine, thioguanine, azathioprine, tiamiprine, vidarabine, pentostatin and puromycin.

Examples of natural products include vinca alkaloids such as for example vinblastine and vincristine; epipodophylotoxins such as, for example, etoposide, and teniposide; antibiotics such as, for example, adrimycin, daunomycin, dactinomycin, daunorubicin, doxorubicin, mithramycin, bleomycin and mitomycin; enzymes such as, for example, L-asparaginase; biological response modifiers such as, for example, alpha-interferon; camptothecin; taxol; and retinoids such as retinoic acid.

Examples of hormones and antagonists include adrenocorticoids, such as, for example, prednisone; progestins, such as, for example, hydroxyprogesterone acetate, medroxyprogesterone acetate and megestrol acetate; estrogens such as, for example, diethylstilbestrol and ethinyl estradiol; antiestrogens such as for example, tamoxifen; androgens such as, for example, testosterone propionate and fluoxymestrone; antiandrogens such as, for example, flutamide; and gonadotropin-releasing hormone analogs such as, for example, leuprolide.

Examples of miscellaneous agents include anthracenediones such as for example, mitoxantrone; substituted ureas such as, for example, hydroxyureas; and adrenocortical suppressants such as, for example, mitotane and aminoglutethimide.

In addition, the chemotherapy agent can be an immunosuppressive drug, such as, for example, cyclosporine, azathioprine, sulfasalazine, methozsalen and thalidomide.

The chemotherapy agents useful in the practice of the present invention are commercially available or can be prepared by methods known in the art. The chemotherapy agent can be used alone or in combination with one or more chemotherapy agents. For example, a combination of three different chemotherapy agents and one or more of the compounds of Formula I, as defined herein, administered in accordance with the methods of the present invention could be used to treat a cancer tumor.

In the compounds of Formula I,

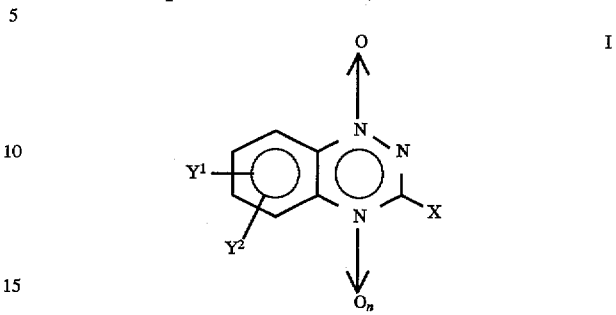

X is hydrogen; unsubstituted branched or straight chain hydrocarbyl (1–4C) such as methyl, ethyl, s-butyl and iso-propyl; hydroxy; alkoxy (1–4C) such as methoxy, ethoxy, propoxy, and t-butoxy; primary amino ($NH_2$); secondary amino (NHR) where R is an alkyl or acyl of 1 to 4 carbons, such as methylamino and ethylamino; tertiary amino (NRR) where each of the R groups is an alkyl or acyl of 1 to 4 carbons, for example diethylamino and the like, or the two R's join to form a morpholino, pyrrolidino or piperidino ring. In the case of the various alkyl and acyl R groups, they can be further substituted with OH, $NH_2$, lower alkyl (1–4C) secondary amino and dialkyl (1–4C) tertiary amino, morpholino, pyrrolidino, piperidino, alkoxy (1–4C) or halogen (fluoro, chloro, bromo or iodo) substituents.

The hydrocarbyl X groups can be further substituted with OH, $NH_2$, alkyl secondary amino, dialkyl tertiary amino alkoxy (1–4C) or halogen (fluoro, chloro, bromo or iodo) substituents.

More preferably X is hydrogen, primary amino ($NH_2$); unsubstituted branched or straight chain hydrocarbyl (1–4C) or substituted branched or straight chain hydrocarbyl (1–4C).

n is 1, preferably 1.

$Y^1$ and $Y^2$ are independently hydrogen; nitro; halogen (e.g. fluoro, chloro, bromo or iodo); or hydrocarbyl (1–4C). When hydrocarbyl, $Y^1$ or $Y^2$ may be saturated or unsaturated, cyclic or acyclic, and may optionally be interrupted by a single ether linkage. Thus, the unsubstituted hydrocarbyl forms of $Y^1$ or $Y^2$ can be, for example, methyl, ethyl, n-propyl, s-butyl, n-hexyl, 2-methyl-n-pentyl, 2-ethoxyethyl, 3-(n-propoxy)-n-propyl, 4-methoxybutyl, cyclohexyl, tetrahydrofurfuryl, furfuryl, cyclohexenyl, 3-(n-decyloxy)-n-propyl, and 4-methyloctyl, 4,7,-dimethyloctyl.

The hydrocarbyl $Y^1$ and $Y^2$ groups may optionally be substituted with 1 or 2 substituents selected from halogen such as fluoro, chloro, bromo or iodo; hydroxy; epoxy; alkoxy (1–4C) such as, for example, methoxy, n-propoxy and t-butoxy; alkyl thio; (1–4C) primary amino ($NH_2$); morpholino; pyrrolidino; piperidino; secondary amino (NHR') where R' is a 1–4C alkyl, such as methylamino, propylamino and the like; tertiary amino (NR'R'); acyloxy and acylamido groups represented by R'COO— and R'CONH—, respectively, and their thiol analogs represented by R'CSO— and R'CSNH-respectively; carboxy (—C(O)OH); alkoxycarbonyl (—C—(O)OR'); carbamyl (—C(O)$NH_2$); alkylcarbamyl (1–4C) (—C(O)NHR'); alkylsulfonyl (1–4C) ($R'SO_2$—); and alkyl phosphonyl (1–4C) (R'P(OR')O—).

In addition $Y^1$ and $Y^2$ can each independently be —$NH_2$, —NHR', —NR'R', —OCOR', —NH(CO)R', —O(SO)R' or —O(ROR')R" in which the various R' groups are lower alkyls (1–4C) which themselves may be substituted with OH, $NH_2$, alkyl secondary and tertiary amino, pyrrolidino, piperidino, alkoxy (1–4C), or halogen substituents.

More preferably, $Y^1$ and $Y^2$ are independently H, nitro, carboxy, alkoxycarbonyl, alkylsulfonyl or —NHR' wherein R' is —$CH_2$—$(CH_2)_m$—$CH_2$—$NR_1R_2$, $R_1$ and $R_2$ are independently selected from the group consisting of hydrogen, lower alkyl, or the $R_1$ and $R_2$ groups may be linked to form a piperidino or pyrrolidino ring, and m is an integer from 0 to 4, preferably 1 or 2.

Particularly preferred compounds of Formula I for use in the present invention include 1,2,4-benzotriazine 1,4-dioxide (wherein X is hydrogen, $Y^1$ and $Y^2$ are each hydrogen and n is 1); 3-amino-1,2,4-benzotriazine 1,4-dioxide (i.e., tirapazamine, SR 4233, wherein X is $NH_2$, $Y^1$ and $Y^2$ are each hydrogen and n is 1); 3-ethyl-1,2,4-benzotriazine 1,4-dioxide (wherein X is ethyl, $Y^1$ and $Y^2$ are each hydrogen and n is 1); 3-propyl-1,2,4-benzotriazine 1,4-dioxide (wherein X is propyl, $Y^1$ and $Y^2$ are each hydrogen and n is 1) and; 3-(1-hydroxyethyl)-1,2,4-benzotriazine 1,4-dioxide (wherein X is 1-hydroxyethyl, $Y^1$ and $Y^2$ are each hydrogen and n is 1); most particularly 3-amino-1,2,4-benzotriazine 1,4-dioxide.

Pharmaceutically acceptable salts of the compounds of Formula I, as defined herein, include salts formed from inorganic acids such as hydrochloric, hydrobromic, or phosphoric adds; organic adds such as acetic add, pyruvic acid, succinic acid, mandelic acid, and p-toluene sulfonic acid; salts formed from inorganic bases such as sodium, potassium or calcium hyrdoxide or from organic bases such as caffeine, ethylamine or lysine.

The compounds of Formula I, as defined herein, may be administered to patients orally or parenterally (intravenously, subcutaneously, intramuscularly, intraspinally, intraperitoneally, and the like). When administered parenterally the compounds will normally be formulated in a unit dosage injectable form (solution, suspension, emulsion) with a pharmaceutically acceptable vehicle. Such vehicles are typically nontoxic and nontherapeutic. Examples of such vehicles are water, aqueous vehicles such as saline, Ringer's solution, dextrose solution, and Hank's solution and nonaqueous vehicles such as fixed oils (e.g., corn, cottonseed, peanut, and sesame), ethyl oleate, and isopropyl myristate. Sterile saline is a preferred vehicle. The vehicle may contain minor amounts of additives such as substances that enhance solubility, isotonicity, and chemical stability, e.g., antioxidants, buffers, and preservatives. When administered orally (or rectally) the compounds will usually be formulated into a unit dosage form such as a tablet, capsule, suppository or cachet. Such formulations typically include a solid, semisolid or liquid carrier or diluent. Exemplary diluents and vehicles are lactose, dextrose, sucrose, sorbitol, mannitol, starches, gum acacia, calcium phosphate, mineral oil, cocoa butter, oil of theobroma, alginates, tragacanth, gelatin, methylcellulose, polyoxyethylene, sorbitan monolaurate, methyl hydroxybenzoate, propyl hydroxybenzoate, talc and magnesium stearate.

The chemotherapy agent is administered to the mammal by conventional routes appropriate for the particular chemotherapy agent. The chemotherapy agent and the compound of Formula I, as defined herein, can be administered by the same route, or by different routes, depending on the particular combination of compound of Formula I, as defined herein, and chemotherapy agent. The compound of Formula I, as defined herein, can be administered to the mammal alone or in combination with one or more other compounds of Formula I, as defined herein.

The compounds of Formula I, as defined herein, are administered to the mammal in amounts effective to kill or produce cytotoxic effects upon hypoxic tumor cells. The amount of the compound administered will depend on such factors as the type of cancer minor, the age and health of the mammal, the maximum tolerated and/or lethal dosage of the chemotherapy agent and the compound of Formula I, and the interaction of the compound of Formula I with the chemotherapy agent. In a presently preferred embodiment of the invention, tirapazamine is administered in amounts of from about 10 $mg/m^2$ to about 450 $mm/m^2$, more preferably from about 20 $mg/m^2$ to about 350 $mg/m^2$; most preferably from about 30 $mg/m^2$ to about 250 $mg/m^2$. When the compound of Formula I is administered to the mammal in divided doses, the lower dosage range may be preferably; depending on the maximum tolerated dosage of the compound and the interaction of the compound with the chemotherapy agent.

The chemotherapy agent is administered to the mammal in amounts effective to treat susceptible tumors. Such amounts are well-known in the art and can be ascertained by reference to product literature furnished by the supplier of the chemotherapy agent or scientific literature. In preferred embodiments of the invention, the chemotherapy agent and the compound of Formula I have a synergistic interaction upon the rumor and it may be possible to administer the chemotherapy agent at doses that are lower than doses recognized as effective when the chemotherapy agent is administered alone. Such lower dosages may be desirable if the chemotherapy agent produces severe side effects in the mammal to which it is administered. If the chemotherapy agent is to be administered to the mammal in divided doses, sufficient amounts of the compound of Formula I, as defined herein, is administered to the mammal so that the synergistic effect of the combination of two agents is maintained, whether before the initial dose of the chemotherapy agent or prior to each individual dose of the chemotherapy agent. The methods of the invention can also be employed in conjunction with other types of cancer treatments such as radiation therapy and surgical removal of the tumor.

The compound of Formula I is administered to the mammal from about one half hour to about twenty-four hours prior to administration of the chemotherapy agent. Alteratively, the compound of Formula I can be administered to the mammal from about one to about two hours after the administration of the chemotherapy agent. For some combinations of chemotherapy agent and compound of Formula I it may be possible to administer the compound of Formula I more than twenty-four hours prior to administration of the chemotherapy agent and still retain the advantages of the methods of the present invention. The time differential providing the most advantageous increase in cell toxicity can be determined by testing the combination of compound of Formula I and chemotherapy agent in in vivo and or in vitro experimental tumor models, such as the one set forth herein, or any other tumor model. The time differential determined in such models is then used as a guide for treatment of minors in mammals, with adjustments made during treatment if necessary. Applicants have found that for the combination of tirapazamine and cisplatin, the greatest interaction between the two agents was observed when tirapazamine was administered between about one and three hours prior to administration of the cisplatin, with the greatest increase in cell death occurring when tirapazamine was administered about two and one half hours prior to cisplatin. When tirapazamine was administered one to two hours after administration of cisplatin, an enhanced cytotoxic effect was observed, however, the increase was not as large. In some embodiments of the invention, it may be desirable to administer the compound of Formula I at the same time as the chemotherapy agent.

The present invention also provides kits for treatment of mammalian tumors comprising at least one chemotherapy agent and at least one compound of Formula I, as defined herein. The compound of Formula I as defined herein is preferably supplied in the kits in cytotoxicity-enhancing amounts or doses. Suitable dosage forms for the compounds of Formula I, as defined herein, are disclosed herein. The particular dosage form of the chemotherapy agent and the compound of Formula I, as defined herein, will be determined by the type of cancer tumor to be treated, the preferred mute of administration and the type of chemotherapy agent. The chemotherapy agent and the compound of Formula I, as defined herein, are preferably supplied in separate containers to facilitate administration of the chemotherapy agent and the compound of Formula I at different times in accordance with the methods of the invention.

The compounds of Formula I useful in the practice of the present invention can be prepared according to the methods disclosed in U.S. Pat. No. 5,175,287 issued Dec. 29, 1992, the disclosures of which are hereby incorporated by reference. General methods for preparing some 3-amino derivatives can be found, for example, in Ley et al., U.S. Pat. No. 3,980,779.

The compounds are prepared from benzofuroxan of the Formula:

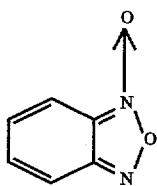

by reaction with a salt of cyanamide, followed by acidification of the reaction mixture. The benzofuroxan starting material is not symmetric with respect to its own 5 and 6 positions (which are the 6 and 7 positions of the resulting 3-amino benzotriazine oxide). Therefore, a mixture of the 6- and 7-substituted materials may result. If desired, this mixture can be separated using conventional means into individual components having a substituent in either the 6 or 7 position.

The dioxide may also be prepared from parent monoxide or 1,2,4-benzotriazine by pencid oxidation (see Robbins et al., J Chem Soc 3186 (1957) and Mason et al., J Chem Soc B 911 (1970)).

In addition, the monoxide may be prepared by:
(1) cyclization of a 1-nitro-2-aminobenzene compound using H$_2$NCN.2HCl;
(2) oxidation of the parent compound given by the structure

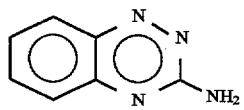

or by controlled reduction of the corresponding dioxide (see Mason, supra, and Wolf et al., J Am Chem Soc 76:355(1954)).

The 1,2,4-benzotriazines may be prepared by cyclization of formazan precursors using BF$_3$/AcOH (see Scheme I and Atallah and Nazer, Tetrahedron 38:1793 (1982)).

3-Amino-1,2,4-benzotriazines may be prepared either by cyclization of a parent compound (see Scheme II and Arndt, Chem. Ber. 3522 (1913)) or by reduction of the monoxide or dioxide as above.

The 3-hydroxy-1,2,4-benzotriazine oxides may be prepared using peroxide and sodium tungstate (Scheme III), a novel synthetic procedure for making the 3-hydroxy-1,4-dioxide compound, or concentrated sulfuric acid and sodium nitrate (Scheme IV).

Scheme II

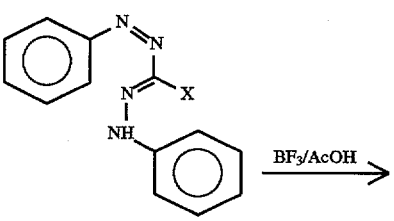

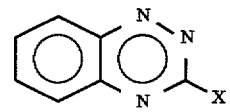

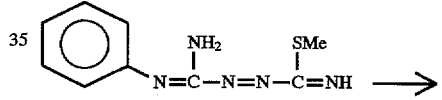

Scheme III

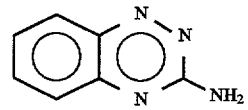

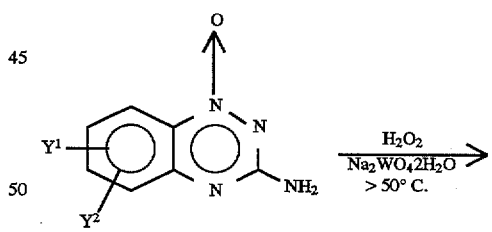

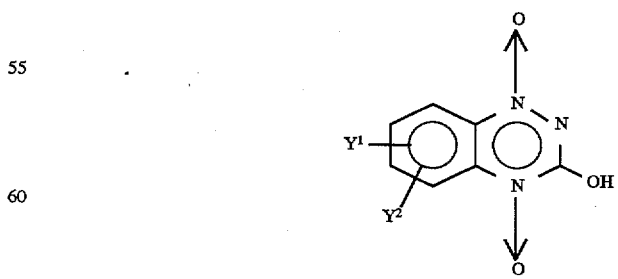

Scheme IV

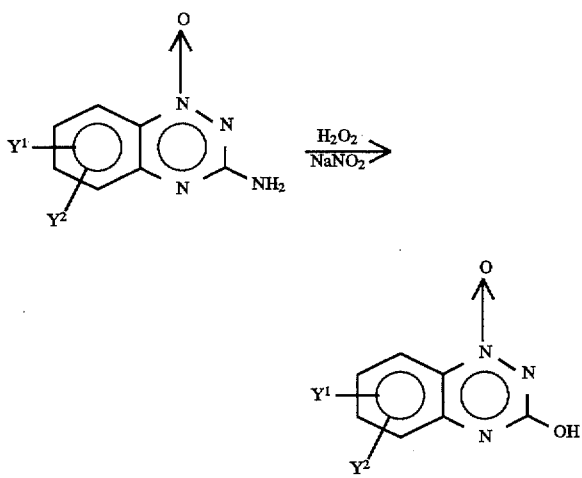

1,2,4-Benzotriazine oxides unsubstituted at the 3 position (sometimes referred to herein as the "3-desamino" compounds) can be prepared by the following method. The method involves treating a 1,2,4-benzotriazine oxide of Formula(I), wherein X is NH₂, with a lower alkyl nitrite under reductive deaminating conditions. By "reductive deaminating conditions" is meant action conditions which will give rise to at least about 10%, preferably at least about 50%, of the desired 3-unsubstituted reaction product. A preferred lower alkyl nitrite for use in said method is t-butyl nitrite. Exemplary reductive deaminating conditions involve action in a compatible solvent, e.g., dimethyl formamide, at a temperature of at least about 60° C., typically at a temperature in the range of 60°–65° C. This reaction is illustrated generally at Scheme V.,

Scheme V

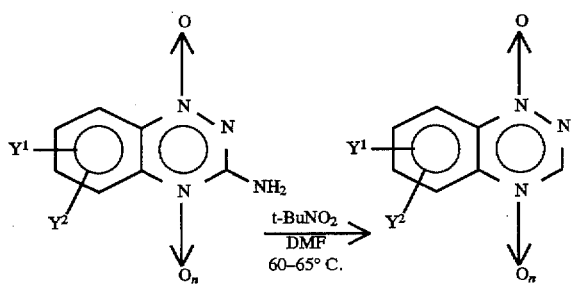

EXAMPLES

The methods of the present invention are exemplified by the following non-limiting examples. Examples 1–18 relate to synthesis of compounds of Formula I, as defined herein. Example 19 relates to in vitro and in vivo tests of tirapazamine and cisplatin.

EXAMPLE 1 Preparation of 3-Hydroxy-1,2,4-Benzotriazine 1,4-Dioxide

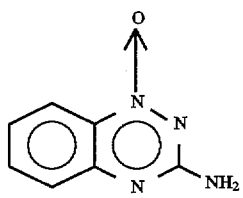

A stirred mixture of 1.50 g (9.25 mmole) of 3-amino-1,2,4- benzotriazine 1-oxide (1), 100.0 ml acid, and 30.0 ml of 30% hydrogen peroxide was treated with 3.05 g (9.25 mmole) of Na₂WO₄·2H₂O. The mixture was stirred in an oil bath at 60° C. for 4 days. The yellowish orange mixture was cooled to about 30° and filtered to remove a light yellow non-UV absorbing solid. The orange solution of hydrogen peroxide in acetic acid was evaporated to semi-dryness carefully with several additions of water and acetic acid to remove most of the peroxide. The concentrated solution was allowed to stand at room temperature to afford four crops of an orange solid, 0.87 g (42% yield of the sodium salt of 2).UV:$\lambda_{max}$ (20% CH₃OH/H₂O): 262.2 (ε39,460); 477 (ε7,030). IR (neat): 3530 m, 3150 m, 2650 m, 2180 m and 1635 m. Anal. (calculated for the sodium salt): C₇H₄N₃O₃Na 1.25H₂O, 223.64: C,37.6; H,2.93; N, 18.79. Found: C,37.8; H,2.75; N, 18.65.

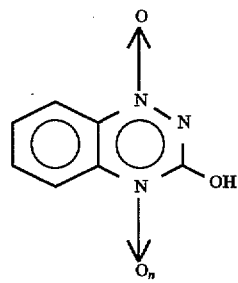

EXAMPLE 2 Preparation of 3-Amino-7-Trifluoromethyl-1,2,4-Benzotriazine 1-Oxide:

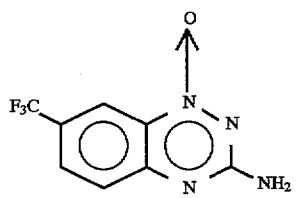

A mixture of 4-chloro-3-nitrobenzotrifluoride (Aldrich, 2.70 g, 12.9 mmole) and cyanamide dihydrochloride (2.75 g, 24 mmole) (previously prepared by treating an ether solution of cyanamide with HCl gas and collecting the precipitated solid) was heated at 140° C. for 1 hour. The residue was treated with 2N NaOH (45 ml), heated for a further 5 min., and then allowed to cool. The precipitate was collected, washed with H₂O, dried, and triturated with acetone-toluene to yield 1.32 g (45%) of 3 as a light yellow solid M.P. 301°–302°. TLC Rf0.60 (9:1 methylene chloride: methanol on silica gel plates). MS: m/z (relative intensity) 230 (100, M⁺).

EXAMPLE 3 Preparation of 3-Amino-7-Decyl-1,2,4-Benzotriazine

13

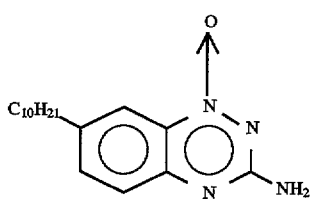

Preparation of 4-(1-decyl)-2-nitroaniline: Acetic anhydride (400 ml) was added over a 30-minute period to a stirred solution of 4-decylaniline (Aldrich, 80 g, 0.34 mole) in hexanes (2.41). After stirring for 1h, the mixture was cooled and treated over 30 min. at 25°–10° C. with 70% nitric acid (34 ml). Stirring was continued at 5°–10° C. for 1 h and at 25° C. for 16h. The mixture was diluted with $H_2O$ (11), stirred for 5h, poured into an open dish and allowed to stand for 16h. After further dilution with $H_2O$ (1.51), the solid was collected and recrystallized from an 85% ethanol solution (in water) to give 92 g (84%) of the intermediate as an orange solid, m.p. 64° C.

A solution (100 ml) of 85% KOH (19 g, 0.288 mole) in $H_2O$ was combined with a suspension of 4-(1-decyl)-2-nitroaniline (89 g, 0.28 mole), prepared above, in methanol (900 ml). The mixture was stirred for 6h, neutralized to pH 7–8 with concentrated HCl, and evaporated in vacuo to near dryness. After dilution with $H_2O$ (400 ml), the solid was collected and air-dried to give 77 g (100%) of the intermediate as an orange solid, m.p. 59° C.

1.0 g (8.7 mmole) of cyanamide dihydrochloride (previously prepared for use by treating an ether solution of cyanamide with HCl gas and collecting the precipitated solid) was added portionwise over 10 min to a preheated melt (190° C.) of 4-(1-decyl)-2-nitroaniline prepared in the preceding step (500 mg, 1.8 mmole). The reaction mixture was heated at 190° C. for 5 min, cooled to 25° C., treated with 6N KOH (10 ml), and heated at 90°–95° C. for 1h. After cooling to 25° C., the solid was collected, washed with $H_2O$ and ethanol and air-dried to give 0.25 g (46%) of compound 4 as a light yellow solid, m.p. 177° C. (dec). MS: m/z (relative intensity) 285 (100, $M^+$), 302 (13)

EXAMPLE 4 Preparation of 3-Amino-7-Carbamyl- 1,2, 4-Benzotriazine 1-Oxide

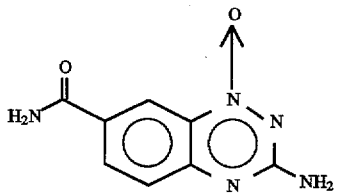

Preparation of 4-chloro-3-nitrobenzamide: 20.2 g (0.1 mole) of 4-chloro-3-nitrobenzoic acid (Aldrich) and thionyl chloride (20 ml) were combined, allowed to stand for 16h, and refluxed for 4h to give a clear red solution. The solution was evaporated in vacuo and azeotroped with benzene. The residue was dissolved in acetonitrile (20 ml) and added over 30 min to cold (−10° C.) concentrated ammonium hydroxide (100 ml). After 3h at −10° C. and 16h at 25° C. the mixture was poured into an open dish and allowed to evaporate to dryness. The residue was slurried in $H_2O$ and the solid was collected and air-dried to give 19.8 g (98%) of the intermediate as a light yellow solid, m.p. 153° C.

A solution of Na(3.45 g, 0.15 mole) in ethanol (75 ml) was added to a solution of guanidine hydrochloride (15.8 g, 0.165 mole) in ethanol (75 ml). After 1h the mixture was filtered and the filtrate was combined with a suspension of 4-chloro-3-nitrobenzamide (10 g, 0.05 mole) prepared above, in ethanol (50 ml). The mixture was stirred and refluxed for 16h, cooled to 0°–5° C., and acidified with concentrated HCl (8 ml). The collected solid was combined with $K_2CO_3$ (28 g, 0.2 mole) and $H_2O$ (40 ml) and the mixture was stirred and heated at 100° C. for 8h. After cooling to 25° C., the solid was collected, washed with $H_2O$, and air-dried. The solid was suspended in boiling ethyl acetate, collected and washed with hot ethyl acetate. The solid was repeatedly suspended in boiling dioxane and collected (6×100 ml). The combined filtrate was evaporated in vacuo to a solid. The solid was suspended in 95% ethanol, collected and air-dried to give 0.44 g (4.3%) of compound 5 as a light yellow solid, m.p. 300° C. TLC: $Rf=0.23$ (methylene chloride: acetone of 2:1, silica gel plates). MS: m/z (relative intensity) 205 (100, $M^+$).

EXAMPLE 5 Preparation of 7-Acetyl-3-Amino-1,2,4-Benzotriazine 1-Oxide Oxime

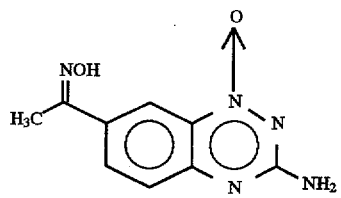

A combined mixture of 7-acetyl-3-amino-1,2,4-benzotriazine 1-oxide (prepared in Example 5; 50 mg, 0.25 mmole), hydroxylamine hydrochloride (200 mg, 2.88 mmole), pyridine (1 ml), and ethanol (1 ml) was heated at 90°–95° C. for 1h and then cooled to 25° C. The mixture was diluted with 95% ethanol (5 ml) and the solid was collected and air-dried to give 30 mg (56%) of compound 6 as a light yellow solid, m.p. 278° C. (dec). TLC: $Rf=0.60$ (9:1 methylene chloride: methanol). MS: m/z (relative intensity) 219 (100, $M^+$).

EXAMPLE 6 Preparation of 3-Amino-6(7)-Decyl-1,2,4-Benzotriazine 1,4-Dioxide

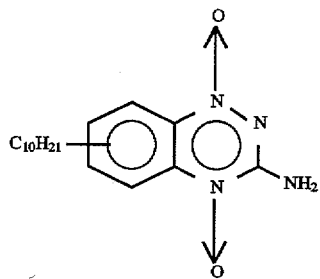

5-(1-decyl)-benzofuroxan: A combined mixture of 4-(1-decyl)-2-nitroaniline (77 g, 0.28 mole), 5.25% NaOCl in $H_2O$ (476 g, 0.34 mole), 85% KOH (20.3 g, 0.31 mole), $nBu_4NHSO_4$ (4.7 g, 0.014 mole), and $CH_2Cl_2$ (2.28 1) was stirred rapidly for 6h and diluted with $H_2O$ (500 ml) and $CH_2Cl_2$ (11). The separated organic phase was washed successively with 1N HCl (11)and brine(2×11)), dried ($Na_2SO_4$),and concentrated in vacuo to yield a red oil, 70 g (92%).

A solution of 5-(1-decyl)-benzofuroxan as prepared above (10 g, 0.036 mole) and benzyltriethyl ammonium chloride (0.36 g, 0.0016 mole) in DMSO (180 ml) was treated gradually over several hours with cyanamide (13.0 g, 0.31 mole) and K$_2$CO$_3$ (36.8 g, 0.27 mole). The mixture was stirred for 48h and filtered. The filtrate was diluted with H$_2$O (61) and glacial acetic acid (40 ml) and extracted with CH$_2$Cl$_2$ (4×500 ml). The combined organic solution was washed successively with 5% NaHCO$_3$ solution (1×500 ml) and brine (2×500 ml), dried (Na$_2$SO$_4$), and evaporated in vacuo to dryness. The crude product was purified by chromatography on silica gel using CH$_2$Cl$_2$: methanol (98.2) to give 1.8 g (16%) of compound 7 as a red solid, m.p. 155° C. (dec). MS: m/z (relative intensity) 318 (4, M$^+$), 285 (100).

EXAMPLE 7 Preparation of 1,2,4-Benzotriazine Dioxide

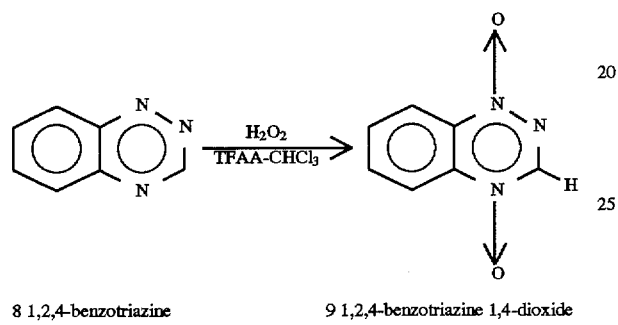

8 1,2,4-benzotriazine      9 1,2,4-benzotriazine 1,4-dioxide

A mixture of 1.80 g (13.73 mmole of 90% H$_2$O$_2$ (9 ml), trifluoroacetic anhydride (13.5 ml) and Na$_2$WO$_4$.2-H$_2$O (12.50 g, 38 mmole) in CHCl$_3$ (170 ml) was stirred at room temperature for 5 days. The reaction mixture was diluted with H$_2$O (100 ml) and extracted with CHCL$_3$ (100 ml). The organic layer was washed with H$_2$O (50 ml), dried (Na$_2$SO$_4$), and the solvent removed in vacuo. The residue was chromatographed on silica gel using EtOAcCH$_2$Cl$_2$ (1:1) to give 0.30 g (13.4%) of compound 9 as a yellow solid, m.p. 204°–205° C. Anal. Calc'd. for C$_7$H$_5$N$_3$O$_2$ (163.13): C, 51.5; H, 3.09; N, 25.76. Found: C, 51.6; H, 3.36; N, 26.01. MS: m/z (relative intensity) 163 (100, M$^+$), 147 (50). TLC: R$f$=0.27 (EtOAc-CH$_2$Cl$_2$, 1:1, silica gel plates). IR (nujol): 1600μ, 1460μ, 1300μ, UV:λ$_{max}$ (H$_2$O): 227 (e22,900) 252 (e12,950): 392 (e4,080).

EXAMPLE 8 Preparation of 7-Chloro-3-Hydroxy-1,2,4-Benzotriazine 1,4-Dioxide

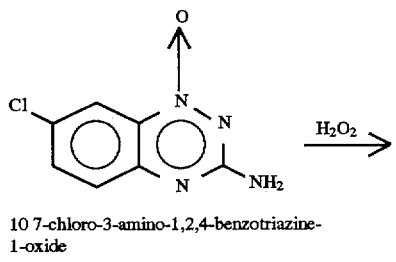

10 7-chloro-3-amino-1,2,4-benzotriazine-1-oxide

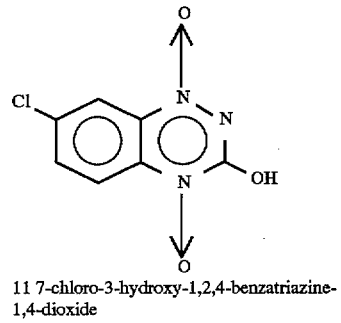

11 7-chloro-3-hydroxy-1,2,4-benzatriazine-1,4-dioxide

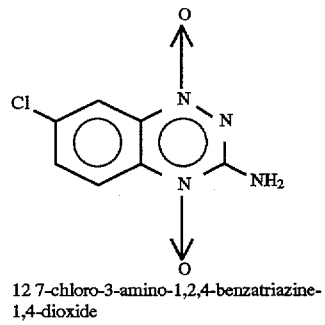

12 7-chloro-3-amino-1,2,4-benzatriazine-1,4-dioxide

A mixture of 1.50 g (7.63 mmole) of 10 in 100 ml acetic acid was treated with 2.52 g (7.63 mmole) of Na$_2$WO4.2H$_2$O and 30 ml of 30% H$_2$O$_2$. The mixture was stirred and heated for 6 days at 50° C., then slowly evaporated to dryness to remove H$_2$O$_2$. The residue was boiled in 250 ml H$_2$O and filtered to remove about 25 mg of starting material 10. The aqueous solutions were then extracted with 2×250 ml potions of ethyl acetate. A deep red crystalline material that was characterized as 12 by TLC and Mass. Spec. analysis formed in the partitioning mixture above and was collected by filtration to afford 60.0 mg of a yellowish orange solid (3.7% yield), characterized as follows as 12, which showed good solubility in a mixture of hot isopropyl alcohol and water. Mass. Spec.: M$^+$=212 (q=100)(compound 10); TLC: R$f$=0.34 (acetone, silica gel plates).

The ethyl acetate solutions above, separated from the H$_2$O layer after the filtration to remove 12, were evaporated to dryness. The residue was then treated with isopropyl alcohol at room temperature to afford a dull orange solid, 0.41 g (25% yield) of 11. Mass. Spec.: M$^+$=213 (q=70); TLC: R$f$=0.22 (acetone, silica gel plates). Compound 11 was characterized as the ammonium salt, C$_7$H$_4$ClN$_3$O$_3$NH$_3$, m.w. 230.61, as follows. The free add 11 was dissolved in concentrated NH$_4$OH and then chilled in ice and filtrated to remove a trace of insoluble 12. The red filtrate and washings were evaporated to dryness, leaving a reddish-orange solid. The solid was treated with 50 ml of boiling 1,2-dimethoxyethane, collected on a filter and washed with an additional 25 ml of hot 1,2-dimethyl ether. The solid was dried over P$_2$O$_5$ at 56° C.1/1.0 mm, leaving 0.244 g (87% yield) of 13

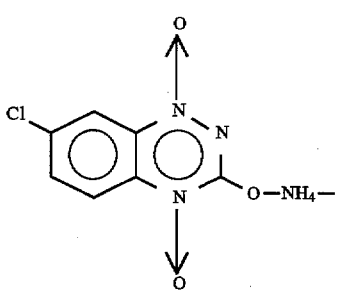

Anal. Calc'd. for $C_7H_4ClN_3O_3NH_3$ (230.61): C, 36.5; H, 306; N 24.30 Found: C 36.5; H13.07; N 23.94 UV:$\lambda_{max}$ ($H_2O$): 219 ($\epsilon$12,580); 265.4 ($\epsilon$40,000); 4830486 ($\epsilon$6,640).

EXAMPLE 9 Preparation of 7-Nitro-3-Amino-1,2,4-Benzotriazine 1,4-Dioxide

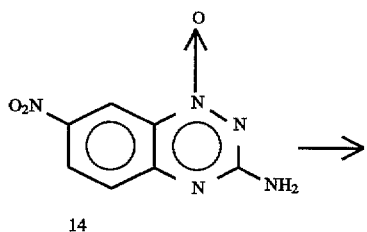

14

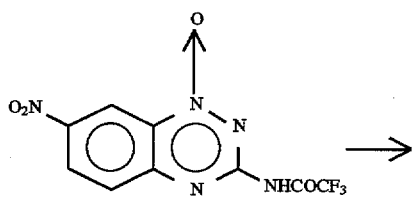

15

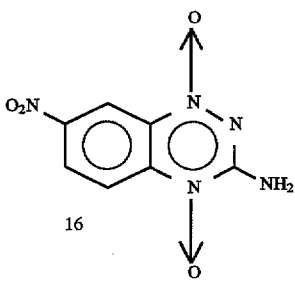

16

7-Nitro-3-trifluoroacetamido-1,2,4-benzotriazine 1-oxide (15): A solution of 7-nitro-3-amino-1,2,4-benzotriazine 1-oxide (4.00 g, 19.3 mmol; Parish Chemical Co.), $CHCl_3$ (125 ml) and trifluoroacetic anhydride (12.0 ml, 85.0 mmol) was stirred at room temperature for 44 hr. The resultant light yellow solid was faltered, washed with $CHCl_3$ (50 ml) and dried to give 5.35 g (91% yield) of the product as a yellow solid. Anal. Calc'd. for $C_9H_4F_3N_5O_4$: C, 35.7; H, 1.33; N, 23.10. Found: C, 35.7; H, 1.23; N, 23.06.

7-Nitro-3-amino-1,2,4-benzotriazine 1,4-oxide (16): To a stirred solution of 7-nitro-3-trifluoroacetamido-1,2,4-benzotriazine 1-oxide prepared above (15)(2.50 g, 8.25 mmol) in $CHCl_3$ (200 ml) was added $Na_2WO_4.2\ H_2O$ (90 mg, 0.273 mmol) followed by 70% $H_2O_2$ (10 ml). After 15 min the solution was treated with trifluoroacetic anhydride (8.0 ml, 56.7 mmol) and stirring was continued at room temperature for 64 hr. The reaction mixture was chromatographed (EtOAc, 20% MeOH/acetone, and finally 20% DMF/acetone) then recrystallized in acetone to give 1.20 g (65% yield) of the product (16) as an orange solid, mp 286°–288° C. (dec.). UV:$\lambda_{max}$ 259, 300, 345, 387, 472. Anal. Calc'd. for $C_7H_5N_5O_4$ C, 37.70; H, 2.26; N, 31.39. Found: C, 7.70; H, 2.13; N, 30.94.

EXAMPLE 10 Preparation of 3-(3-N,N-Diethylaminopropylamino)-1,2,4-Benzotriazine 1,4-Dioxide

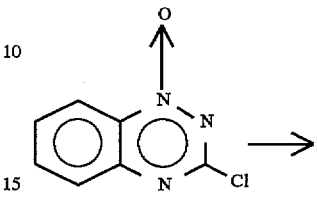

17

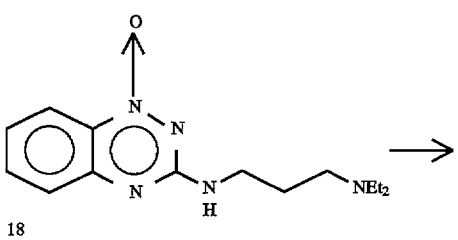

18

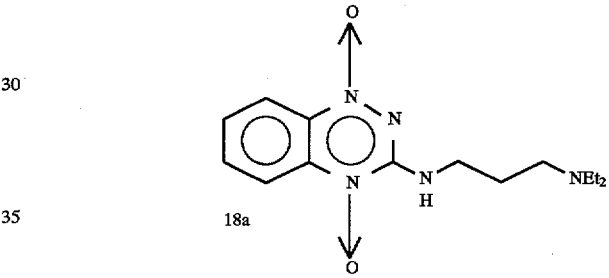

18a 3-(3-N,N-diethylaminopropylamino)-1,2,4-benzotriazine 1-oxide (18): A solution of 3-chloro-1,2,4-benzotriazine 1-oxide (17)(3.0 g, 16.5 mmol) (produced by the method of Sasse et al., U.S. Pat No. 4,289,771) in $CH_2Cl_2$ (100 ml) was treated with N,N-diethyl-propylenediamine (9.5 ml, 88.3 mmol). After 20 hr at room temperature the mixture was diluted with 1,2-dichloroethane (50 ml) and washed successively with $Na_2CO_3$ and $H_2O$. The yellow solution was dried ($Na_2SO_4$), filtered and evaporated in vacuo to give 3.93 g (87% yield) of the product as a yellow Solid. Recrystallization (ether/petroleum ether) yielded pure material, m.p. 47°–48° C. Anal. Calc'd. for $C_{14}H_{21}N_5O$ (18): C, 61.10; H, 7.69; N, 25.44. Found: C, 61.30; H, 7.80; N, 25.61.

3-(3-N,N-diethylaminopropylamino)-1,2,4-benzotriazine 1,4-oxide ( 18a): To a stirred solution of 3-(3-N,N-diethylaminopropylamino)-1,2,4-benzotriazine 1-oxide 18 prepared as above ((1.60 g, 6.10 mmol) in $CHCl_3$ (50 ml) was added trifluoroacetic anhydride (22.0 ml). After 15 min the mixture was cooled to $-10°$ C., 70% $H_2O_2$ (10 ml) added and then stirred at room temperature for 20 days. The reaction mixture was dried ($Na_2SO_4$), filtered and evaporated to dryness. The residue was dissolved in saturated $NaHCO_3$ solution (50 ml) and extracted with $CH_2Cl_2$ (3×150 ml). The organic layer was dried ($Na_2SO_4$), filtered and evaporated to give the product 18a, 0.51 g (29% yield) as a red solid. m.p. 92°–94° C. NMR: $\delta$ (400 MHz, $CDCl_3$) 1.11 (6H, t, J=7.1 Hz, 1.84–1.90 (2H, m, H-2'), 2.48–2.64 (4H, m, $NCH_2CH_3$ and H-3'), 3.68 (2H, br t, J=5.5 Hz, H-1'), 7.46 (1H, ddd, J=7.1, 7.0 and 1.2 Hz, H-6), 7.84, ddd, J=7.0, 6.9 and 1.2 Hz, H-7), 8.31 (2H, m; H-5 and 8), 8.80 (1H, br s, NH), UV:$\lambda_{max}$ 220, 270, 476. Anal. Calc'd. for $C_{14}H_{21}N_5O_2$. (1/3 $H_2O$ ): C, 56.50; H, 7.34; N, 23.55. Found: C, 56.90; H, 7.15; N, 23.40.

EXAMPLE 11 Preparation of 7-Nitro-3-(2-N,N-Diethylaminoethylamino)-1,2,4-Benzotriazine 1,4 Dioxide

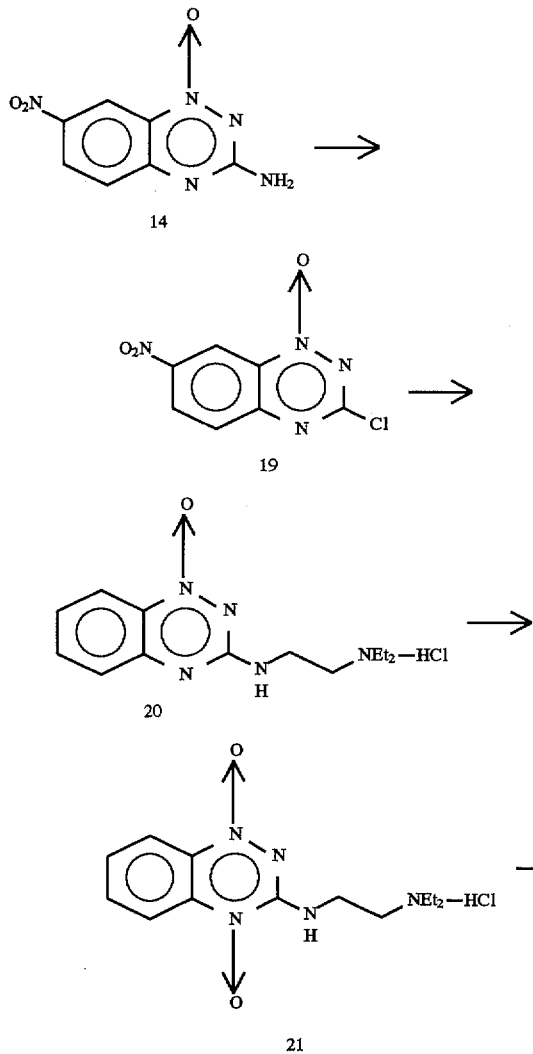

7-Nitro-3-(2-N,N-diethylaminoethylamino)- 1,2,4-benzotriazine 1-oxide hydrochloride (20): A solution of 7-nitro-3-chloro- 1,2,4-benzotriazine 1-oxide 919)( 1.60 g, 7.06 mmol) (prepared as generally shown in Sasse et al, U.S. Pat. No. 4,289,771, with (a) $NaNO_2$ and $H_2SO_4$ at 40° C., followed by (b) chorination with $POCl_3$ at 106° C.) in $CH_2Cl_2$ (50 ml) was treated with N,N-diethylethylenediamine (6.0 ml, 42.7 mmol). After 6 hr at room temperature the mixture was evaporated to dryness under high vacuum at 60° C. The yellow solid was stirred in 20% iPrOH/ether (150 ml) for 5 hr, filtered, washed with iPrOH then petroleum ether and dried (80° C./1.0 mmHg) to give 1.80 g (74% yield) of the product 20 as yellow needle crystals. NMR δ (90 MHz, $d_6$-DMSO/$d_4$-MeOH) 1.25 (6H, t, J=6.0 Hz, $CH_3$), 3.25 (6H, m, $NCH_2$), 3.82 (2H, m, H-1'), 7.74 (1H, d, J=7.0 Hz, H-5), 8.52 (1H, dd, J=7.0 and 2.0 Hz, H-6), 8.91 (1H, d, J=2.0 Hz, H-8).

7-Nitro-3-(2-N,N-diethylaminoethylamino)-1,2,4-benzotriazine 1,4-dioxide hydrochloride (21): To a stirred solution of 7-nitro-3-(2-N,N-diethylaminoethylamino) 1,2,4-benzotriazine 1-oxide (20; prepared as described above) (0.50 g, 1.46 mmol) in $CHCl_3$ (50 ml) at 0° C. was added trifluoroacetic anhydride (9.0 ml). After 30 min 70% $H_2O_2$ (4.0 ml) was added and the mixture stirred at room temperature for 3 days, then dried ($Na_2SO_4$), filtered, and evaporated in vacuo to dryness to give the trifloroacetate salt 0.67 g (45% yield). This product was dissolved in sainted $NaH-CO_3$ solution (30 ml) and extracted with $CH_2Cl_2$ (3×30 ml). The dichloromethane was washed with $H_2O$, dried ($Na_2SO_4$), filtered, saturated with gaseous HCl and evaporated to dryness to give 0.35 g (63% yield, 28% overall) of the product as a red solid, m.p. 194°–195° C. UV:$\lambda_{max}$ 260, 306, 388, 479. Anal. Calc'd. for $C_{13}H_{18}N_6O_4HCl$: C, 43.50; H, 5.34; N, 23.43. Found: C, 43.20; H, 5.37; N, 23.11.

The following Examples 12–15 are directed to reductive deamination reactions for preparing compounds of Formula (I) which are unsubstituted at the 3-position, i.e., wherein the substituent "X" is hydrogen.

EXAMPLE 12 Preparation of 1,2,4-Benzotriazine 1,4-Dioxide by Reductive Deamination of 3-Amino-1,2,4-Benzotriazine 1,4-Dioxide

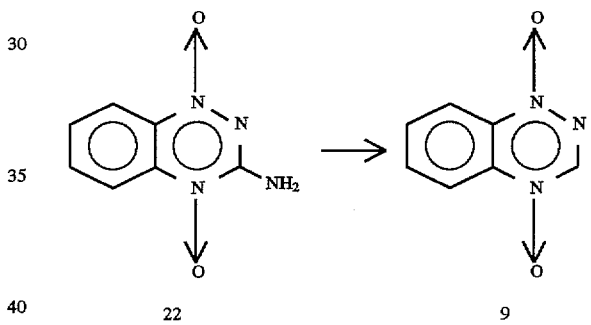

To a rapidly stirred solution of t-butyl nitrite (867 mg, 1.0 ml, 8.41 mmol) in DMF (20 ml) at 60°–65° C. was added 3-amino-1,2,4-benzotriazine 1,4-dioxide ("SR 4233") (500 mg, 2.81 mmol) (prepared by the method of Seng et al., Anqew. Chem. Internal Edit. 11 (1972)) in small potions over 5 min. Following the addition, and subsidence of the concomitant effervescence (approx. 5 min), the solution was collected and reduced under high vacuum to a dark waxy solid. Flash chromatography (30% EtOAc/$CH_2Cl_2$) gave a yellow solid, m.p. 188°–189.5° C. (dec.), which was recrystallized from ethanol to give 195 mg (43% yield) of the product 9 as bright yellow platelets, m.p. 192°–194° C. (dec.). NMR: (400 MHz, d6-acetone) 8.04 (1 H, ddd, J=8.5, 7, 1.5 Hz), 8.15 (1 H, ddd, J=8.5, 7, 1.5 Hz), 8.42 (1 H, dd, J-8.5, 1.5 Hz), 8.43 (1 H, dd, J=8.5, 1.5 Hz) 9.05 (1 H, s, H-3). UV:$\lambda_{max}$ 405, 300, 225.MS: m/z (relative intensity), 147(13), 136(19), intensity) 164(9), 163(100, M+), 147(13), 136(19), 90(7), 78(27), 76(26), 75(8) 64(9), 63(10), 52(12), 5I(48); 50(28), 38(8), 37(5), 30(18), 28(6), 27(7). Anal. Calc'd. for $C_7H_5N_3O2$: C, 51.54; H, 3.09; N, 25.76. Found C, 51.42; H, 3.02; N, 25.66.

EXAMPLE 13 Preparation of 7-Allyloxy-1,2,4-Benzotriazine 1,4-Dioxide Via Reductive Deamination

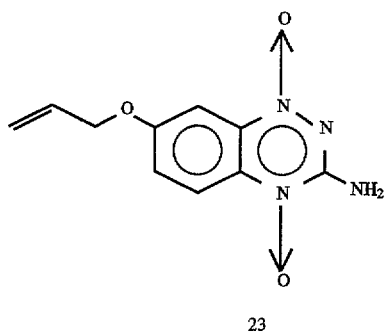

23

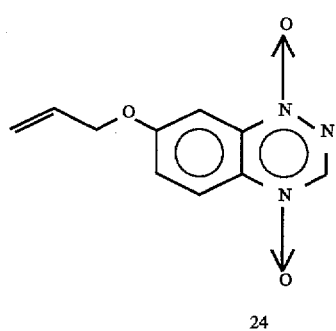

24

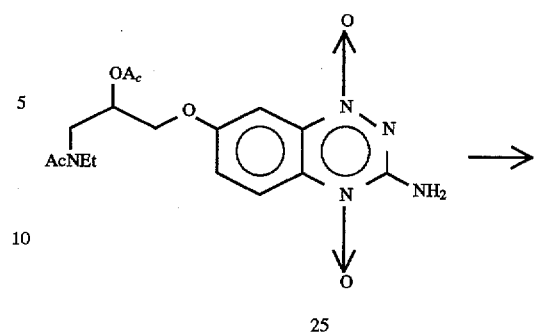

25

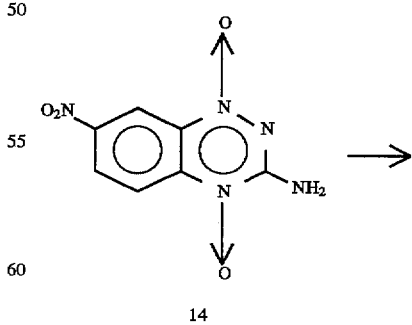

26

7-Allyloxy-1,2,4-benzotriazine 1,4-dixoide (24): To a stirred solution of t-butyl nitrite (271 mg, 0.312 ml, 2.63 mmol) in DMF (15 ml) at 60°–65° C. was added 7-allyloxy-3-amino-1,2,4-benzotriazine-1,4-dioxide 23 (205 mg, 0.875 mmol) in small portions over 5 min. After 30 min additional t-butyl nitrite (271 mg, 0.312 ml, 2.63 mmol) was added, and shortly thereafter the deep red solution effervesced and lightened appreciably in color over a period of a few minutes. After an additional 30 min the resultant orange solution was reduced under vacuum to a brown solid which was sequentially flash chromatographed (10% EtOAc/$CH_2CL_2$) and crystallized ($CH_2Cl_2$/petroleum ether) to give 72 mg (38% yield) of the product 24 as light orange crystals, m.p 147°–148° C. NMR:δ (400 MHz, $d_6$:acetone) 4.89 (2H, ddd, H-1', $J_{1'2}$=5.5, $J_{1'·3'cis}$=$J_{1'·3'trans}$=1.5 Hz), 5.36(1 H, ddd, H-3', $J_{3'·2'cis}$=10.5 $J_{3'·3}$=1.5 Hz), 5.52 (1 H, ddd, H-3', $J_{3'·2'trans}$=17.5, $J_{3'·3}$=3, $J_{3'1}$=1.5 Hz), 6.14 (1 H, ddd, H-2', $J_{2',3'cis}$=10.5, $J_{2'·1}$=5.5 Hz), 7.70 (1 H, d, H-8, $J_{8,6}$=2.5 Hz), 7.74 (1 H, dd, H-6, $J_{6,5}$=9.5, $J_{6,8}$=2.5 Hz), 8.33 (1 H, d, H-5, $J_{5,6}$=9.5 Hz), 8.93 (1 H,s, H-3). UV:$\lambda_{max}$ 425, 410, 365, 355, 320, 245, 200. MS m/z (relative intensity) 220(4), 219(34 M+), 103(4), 77(4), 75(4), 63(13), 62(4), 42(3), 41(100), 39(16). Anal. Calc'd. for $C_{10}H_9N_3O_3$: C, 54.79; H, 4.14; N, 19.17. Found: C, 54.73; H, 4.16; N, 9.15.

EXAMPLE 14 Preparation of 7-(3-N-Ethylacetamido-2-acetoxypropoxy)-1,2,4-Benzotriazine 1,4-Dioxide Reductive Amination To a stirred solution of t-butyl nitrite 9185 mg, 1.79 mmol) in DMF (5 ml) at 60° C. was added via syringe a solution of 7-(3-N-ethylacetamido-2-acetoxypropoxy)-3-amino-1,2,4-benzotriazine 1,4-dioxide () (125 mg, 0.329 mmol) in DMF (5 ml) over a period of 1 min. After 5 min additional t-butyl nitrite (217 mg, 2.10 mmol) was added and an immediate reaction occurred, as evidenced by the evolution of a gas and a change in color of the solution from red to light orange. After an additional 10 min the solution was stripped to a yellow/brown solid and eluted through silica gel with 5% MeOH/$CH_2Cl_2$ to give $CH_2Cl_2$/ligroin gave 90 mg yellow solid (75% yield), m.p. 179°–180.5° C. NMR: δ (400 MHZ, $d_4$-methanol, mixture of rotamers, ratio approx. 2:1) 1.12, 1.22 (Cs, 1:2,3 H total, J=7 Hz), 2.0–6, 2.07 (s's, 2:1, 3 H total), 2.11, 4.34–4.48 (m, 2 H), 5.48–5.58 (m, 1 H), 7.76–7.86 (m, 2H), 8.36–8.42 (m, 1 H), 9.04, 9.06 (s's, 2:1, 1 H total). UV:$\lambda_{max}$ 420, 405, 365, 350, 315, 240, 200. MS: m/z (relative intensity) 365(0.5), 364(1.4, M+), 349(0.5), 348(1.1), 347(0.5), 332(1.2), 331(3.6), 187(7), 186(66), 102(6), 100(21), 84(30), 63(6), 58(100), 56(8), 43(65), 42(9), 41(9), 41(5), 30(14), 29(5), 28(8).

EXAMPLE 15 Preparation of 7-Nitro-1,2,4-Benzotriazine 1,4-Dioxide via Reductive Deamination

14

-continued

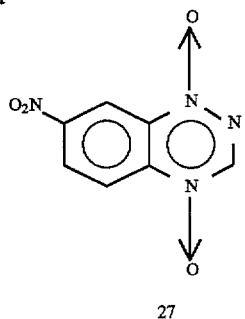

27

To a stirred solution of t-butyl nitrite 988 mg, 0.85 mmol) in DMF (5 ml) at 60° C. was added 7-nitro-3-amino-1,2,4-benzotriazine 1,4-dioxide 103) (38 mg, 0.17 mmol). After 30 min the addition of further t-butyl nitrite (175 mg, 1.70 mmol) to the dark red slurry was immediately followed by a change in coloration and effervescence. After an additional 10 min the orange solution was reduced to a red solid in vacuo and chromatographed with 1% $AcOH/CH_2Cl_2$ to give 3 mg of the product 27 as a yellow solid (10% yield). NMR δ (90 MHz, $d_6$-dimethyl sulfoxide) 7.68 (d, 1 H, J=9.2 Hz), 7.92 (dd, 1 H, J=9.2, 2.2 Hz), 8.10 (d, 1 H, J=2.2 Hz), 8.65 (s, 1 H). UV:$\lambda_{max}$ 420, 310, 240, 205. MS: m/z (relative intensity) 209(9), 208(100, M+), 192(54), 181(14), 162(16), 105(9), 77(28), 75(52), 74(27), 63(21), 62(16), 30(77), 18(26).

EXAMPLE 16 3-ethyl-1,2,4-benzenetriazine-1,4-dioxide (31)

(TFAA) in $CH_2Cl_2$ gave 3-ethyl-1,2,4-benzenetriazine-1,4-dioxide (31). The title compound 31 was purified using normal-phase column chormatography and recrystallization from aqueous ethanol to give material of 99.8% purity. The melting point of 31 was found to be 141°–142° C.

EXAMPLE 17 3-propyl-1,2,4-benzotriazine-1,4-dioxide (32)

3-propyl-1,2,4-benzotriazine-1,4-dioxide (32) was prepared and purified according to the method of Example 16 (preparation of 3-ethyl-1,2,4-benzenetriazine-1,4-dioxide) except that the hydrazone formed from the condensation of butyraldehyde and phenyl hydrazine was used in the reaction with benezenediazonium instead of the hydrazone formed from the condensation of propionaldehyde and phenyl hydrazine. The melting point of 32 was found to be 114°–116° C.

EXAMPLE 18 3-(1-hydroxyethyl)-1,2,4-benzotriazine 1-oxide

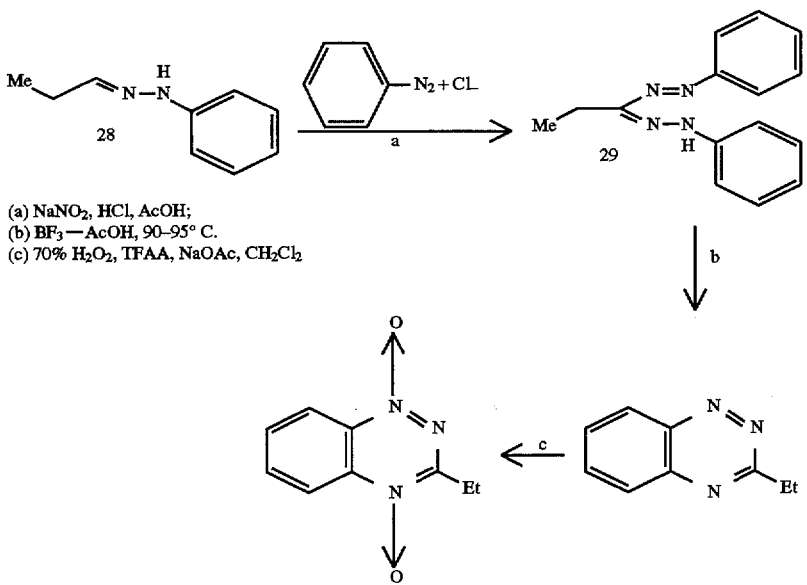

(a) $NaNO_2$, HCl, AcOH;
(b) $BF_3$—AcOH, 90–95° C.
(c) 70% $H_2O_2$, TFAA, NaOAc, $CH_2Cl_2$

The hydrazone (28), formed from the condensation of propionaldehyde and phenyl hydrazine, was reacted with benezenediazonium chloride in a mixture of acetic acid, sodium nitrite and HCl to give the formazan (29). Cyclization with $BF_3$-AcOH (boron trifluoride-acetic acid) at 90°–95° C. gave 3-ethyl-1,2,4-benzenetriazine (30) as an oil, which was purified by distillation. Oxidation with 70% hydrogen peroxide and trifluoroacetic acid anhydride

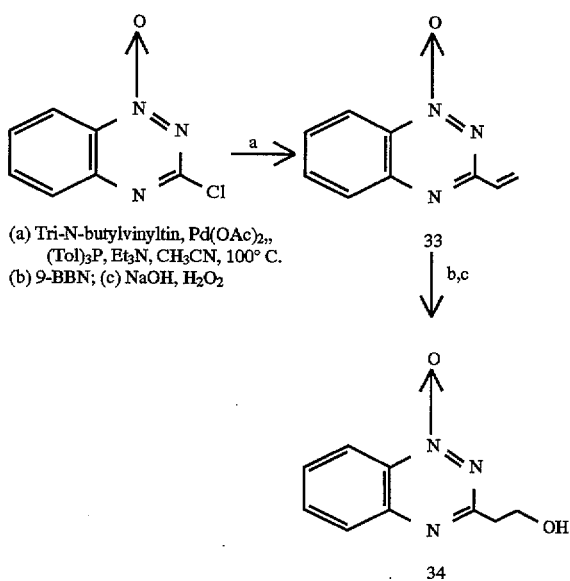

(a) Tri-N-butylvinyltin, Pd(OAc)₂,
(Tol)₃P, Et₃N, CH₃CN, 100° C.
(b) 9-BBN; (c) NaOH, H₂O₂

3-chloro-1,2,4-benzotriazine 1-oxide was treated with a slight excess of tri-N-butylvinyltin in a mixture of acetonitrile, tritoluyl phosgene and triethylamine, using palladium II catalysis (Pd II acetate) in a sealed tube at 100° C. for 48 hours. Removal of solvent and purification by column chromatography gave 3-vinyl-1,2,4-benzotriazine 1-oxide (33). Reduction with 9-borabicyclo [3.3.1] nonane (9-BBN) followed by oxidation with sodium hydroxide and hydrogen peroxide gave the title compound 3-(1-hydroxyethyl)-1,2,4-benzotriazine 1-oxide (34).

EXAMPLE 19

Tirapazamine and cisplatin were tested in an in vivo RIF-1 tumor model. Tirapazamine and cisplatin were also tested in an in vivo assay using RIF-1 cells under hypoxic and aerobic conditions.

Animals and tumors: The RIF-1 fibrosarcoma (developed and maintained in the laboratory of Dr. Martin Brown, Department of Radiation Oncology, Stanford University, Stanford, Calif.; Twentyman et at. I. Nail Cancer Inst. 64: 595–604) in C3H/Km mice (bred and maintained by the Radiation Biology Division at Stanford University Medical School) housed under defined flora conditions, was maintained alternately in vivo and in vitro, according to a previously published protocol (Twentyman, supra). Tumor cell monolayers, growing in Waymouth's medium supplemented with 15% fetal calf serum, were harvested with 0.05% trypsin. From this suspension, 2×10⁵ cells in 0.05 ml medium were inoculated intradermally in the back of each mouse at a site approximately 2 cm above the tail. Experiments were begun two weeks later when the mean tumor volume was approximately 200 mm³.

Drugs: Tirapazamine (SR 4233) was supplied by Sterling Drug Inc (New York, N.Y.). For animal studies, the drag was dissolved in normal saline at a concentration of 1 mg/ml and injected intraperitoneally (i.p.) on a mmol/kg basis. Cisplatin (c-DDP) from Bristol Laboratories (Princeton, N.J.) was dissolved in sterile water and injected i.p. in 0.01 rot/gin body weight.

Cell Survival: For animal studies, RIF- 1 cell survival was evaluated according to an in vivo/in vitro excision assay. Toward this end, mice were killed 24 hours after cisplatin treatment; tumors were excised, minced, and dissociated with an enzyme cocktail (Twentyman supra) and cells were plated for clonogenic assay. Resultant tumor cell colonies were stained with crystal violet and counted after two weeks incubation at 37C in a 5% $CO_2$ humidified atmosphere. Relative clonogenic cells per tumor was calculated as the product of plating efficiency and tumor cell yield for treated tumors relative to that for control untreated tumors assayed in parallel.

For the studies on cells in vitro, RIF-1 cells were seeded into 60 mm glass petri dishes in Waymouth's medium supplemented with 15% fetal bovine serum at a concentration of 2×10⁴ cells per dish. The experiments were performed 4 to 5 days later when there were approximately 10⁶ cell per dish at the time of treatment. The growth medium was then replaced with 2 ml of medium without serum containing tirapazamine at a concentration of either 2 or 4 µg/ml. In each experiment, groups were included in which treatment with tirapazamine and cisplatin were performed both simultaneously and with an interval between the two treatments. In those groups in which there was an interval immediately after the exposure to tirapazamine, the cells were rinsed twice and fie medium replaced with full growth medium until the time for the second treatment (with cisplatin), which was also performed in medium without serum. Both the exposure to tirapazamine and to cisplatin were for one hour under hypoxic conditions. To achieve hypoxia, the dishes were loaded into specially fabricated, prewarmed aluminum gassing chambers which were placed in a shaking table and connected to a gassing manifold comprising a vacuum outlet line and inlet lines for air or nitrogen (+5% $CO_2$). Hypoxia was achieved in the aluminum chambers through a series of 5 alternate evacuations in 2 to 3 minutes to 0.1 atmosphere followed by gassing with nitrogen (+5% $CO_2$). After gassing, the chambers were sealed and incubated for one hour at 37C. Measurement of the oxygen level in the medium using a Clarke electrode showed that hypoxia was achieved rapidly (in approximately 10 minutes with an average $pO_2$ level during the one hour exposure of less than 200 parts/million oxygen). Immediately after the treatment with cisplatin, the cells were trypsinized, counted and replated in plastic petri dishes in Waymonth's medium supplemented with 15% fetal bovine serum and incubated for 14 days at 37C in a 5% CO2 humidified atmosphere, after which the colonies were stained with crystal violet and counted.

Normal Tissue: The response of normal tissue to tirapazamine and cisplatin was evaluated in the kidney and bone marrow through blood urea nitrogen (BUN) assays and peripheral white cell counts. Blood samples were taken from tail veins or by cardiac puncture. No anticoagulants were used. Peripheral white cell counts for individual mice were determined from 20 µl whole blood diluted in 0.280 ml 3% acetic acid. For serum BUN assays, blood from two mice was pooled, coagulated, vortexed, and centrifuged at 830 g for 15 minutes. After the serum was aspirated, BUN values were determined by a commercial clinical veterinary laboratory. Survival to 30 days was also recorded in another experiment.

Results:

(a) Results on tumors in vivo: FIG. 1 shows the pooled results from two experiments in which 0.35 mmol/kg tirapazamine (63 mg/kg) was delivered to the tumor-bearing mice at various times over an interval from 3 hours prior to 2 hours after delivery of 8 mg/kg cisplatin, and clonogenic survival was assessed at 24 hours. The x-axis shows the relative number of clonogenic cells per tumor, The y-axis shows the time of administration of tirapazamine relative to administration of cisplatin (−2 hours represents data obtained form mice injected with tirapazamine two hours before the cisplatin injection).

Open circles represent tirapazamine alone; open squares represent cisplatin alone; closed squares represent tirapazamine and cisplatin. As shown in FIG. 1, when tirapazamine is administered at intervals between three hours prior to or one to two hours after cisplatin, the relative numbers of clonogenic cells per tumor decreases from about 10-4 to about 10-7. These figures represent a 10-fold to a 1,000-fold decrease in the number of clonogenic cells per rumor in comparison with the number of clonogenic cells per minor when tirapazamine is administered at the same time as cisplatin. The synergistic effect of tirapazamine and cisplatin was most pronounced when tirapazamine is administered from about three hours to one hour prior to cisplatin, with the greatest interactive effect being seen at two and one half hours prior to administration of cisplatin.

Figure 2:
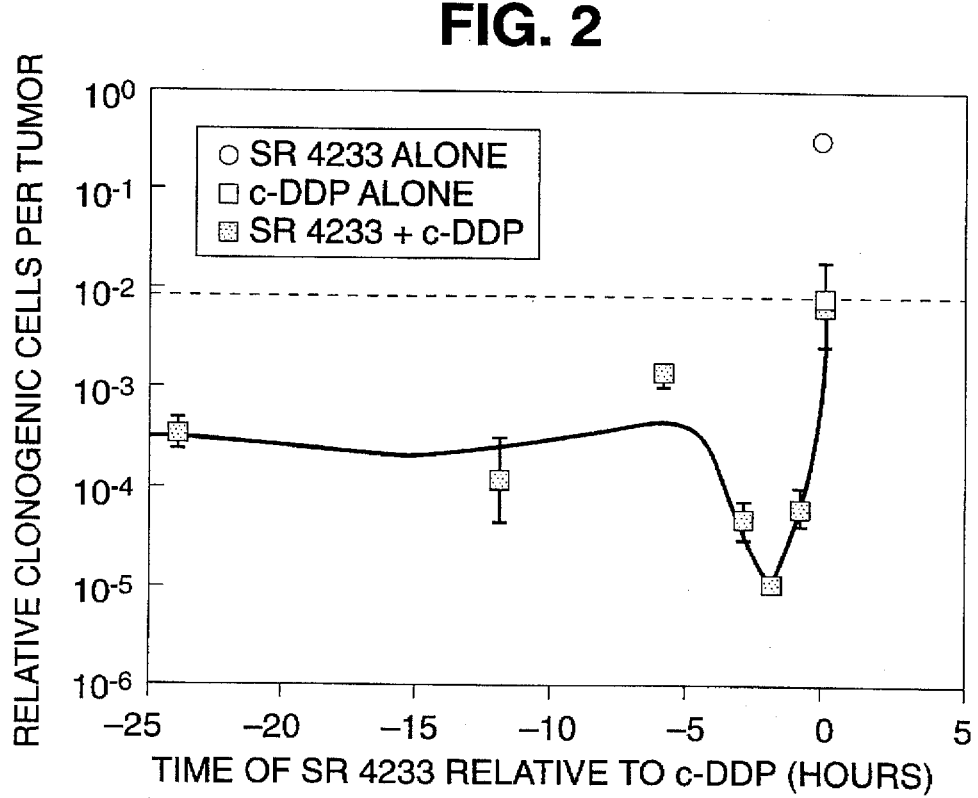
FIG. 2 shows a graph of the relative clonogenic cells per tumor present in experimental RIF-1 tumors versus time (−24 to 0 hours) of administration of tirapazamine relative to cisplatin.

Because of the large amount of cell killing observed at the nadir in FIG. 1 (which was on the border of the limits of the clonogenic assay), the dose of tirapazamine in the experiment was reduced from 0.35 mmol to 0.27 mmol/kg (48.6 mg/kg) and the experiments were repeated. In this experiment, the time gap between administration of cisplatin and tirapazamine was extended to twenty-four hours. The results of this experiment are shown in FIG. 2. The x- and y-axes are the same as for FIG. 1. Open circles represent tirapazamine alone; open squares represent cisplatin alone; closed squares represent cisplatin and tirapazamine. As shown in FIG. 2, the enhanced interaction between tirapazamine and cisplatin was present when tirapazamine was administered up to twenty-four hours prior to cisplatin.

Despite the reduction in amount of tirapazamine administered in the second set of experiments, the data from the three experiments show the same results: essentially additive toxicity when the drugs are given together, and a major cytotoxic interaction when the drugs are separated in time with the maximal reduction in the number of clonogenic cells per tumor when tirapazamine treatment preceded cisplatin by approximately 2.5 hours.

Additional experiments were performed with various doses of tirapazamine given 2.5 hours before either 4 or 8 mg/kg cisplatin. There was an approximately exponential reduction in tumor cell survival at both doses of cisplatin with increasing dose of tirapazamine.

(b) Results on Normal Tissue: Preliminary studies using C3H mice indicated that white cell counts reached a nadir on the third day after treatment with tirapazamine and cisplatin and then rose again to near control levels on day five. A dose response study was therefore done on day 3 of cisplatin alone and tirapazamine plus cisplatin with the tirapazamine dose (0.35 mmol/kg) given 2.5 hours before cisplatin. Cisplatin was administered at three different dose levels—10, 14, and 18 mg/kg. Both tirapazamine and cisplatin produced a mild leukopenia and the combination produced an affect equal to that predicted from adding the responses to the individual drugs.

Assays of serum BUN were performed on the sixth day after injection of tirapazamine and cisplatin, based on a preliminary investigation of the time for maximum increase in BUN following high doses of cisplatin. BUN in C3H mice six days after a single injection of tirapazamine (0.27 mmol/kg), cisplatin (10, 14, or 18 mg/kg) or the two drugs given together (with tirapazamine injected two and one half hours before the cisplatin injection). BUN levels for doses of 10 and 14 mg/kg cisplatin alone were similar to BUN levels for untreated mice (approximately 30 mg/dl). However, 18 mg/kg cisplatin alone had a BUN level of about 80 mg/dl. By contrast, at each dose of the combination of drugs, the BUN level of the treated mice was less than the BUN levels of untreated mice. These results show that tirapazamine in combination with cisplatin does not add to cisplatin kidney toxicity and may even protect at the highest dose tested.

As a further test of whether tirapazamine enhanced the systemic toxicity of cisplatin, an LD50 experiment was performed with cisplatin alone and cisplatin preceded 2.5 hours before injection by tirapazamine. The LD50 for mice treated with 0.35 mmol/kg tirapazamine plus cisplatin was 17.7 mg/kg (95% confidence limit: 16.8–18.7 mg/kg), as contrasted with that for cisplatin alone which was 17.8 (17.1–18.5 mg/kg).

(c) Results of in vitro experiments

Cells were exposed to a one hour period to tirapazamine (2 or 4 µg/ml) under hypoxic conditions and also exposed to cisplatin (2 µg/ml) for one hour as a function of time later. The concentration of each agent was chosen to produce a similar level of cell killing of hypoxic cells as that with the RIF-1 tumors in vivo: for tirapazamine (0.3 and 0.009 and at 2 and 4 µg/ml, respectively) and for cisplatin ($3.5 \times 10^{-3}$). Each experiment contained groups in which there was no separation between the exposure of the two agents (i.e., tirapazamine and cisplatin were administered simultaneously for one hour under hypoxic conditions), as well as a group in which the two exposures were separated from one to four hours. The results obtained for the drugs given simultaneously were not significantly different from the product of the survivals of the two agents given separately (i.e., compatible with additivity); whereas when the drugs were separated, there was more cell killing by a factor of up to $10^2$. Them is a similar kinetics of enhancement of cell killing as observed in the in vivo results, though the absolute magnitude of the effect of splitting the two doses is less than that observed in vivo To check that the interaction between the two agents depended on the presence of hypoxia, the experiments were repeated with three hours between exposure of the cells to tirapazamine under aerobic conditions and exposure of the cells to cisplatin under hypoxic conditions. In these experiments, there was no cytotoxicity due to the tirapazamine, and there was no potentiation of the cell killing compared to that produced by cisplatin alone in the same experiments.

I claim:

1. A method of treating a mammal having a solid tumor, said mammal in need of such treatment, comprising (a) administering to said mammal an effective amount of a compound having the formula

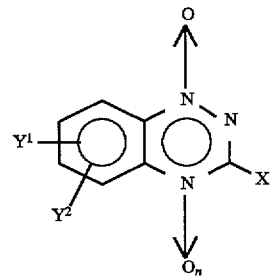

wherein X is $NH_2$;

n is 0 or 1; and $Y^1$ and $Y^2$ are independently either H; nitro; halogen; hydrocarbyl (1–14C) including cyclic and unsaturated hydrocarbyl, optionally substituted with 1 or 2 substituents selected from the group consisting of halogen, hydroxy, epoxy, alkoxy (1–4C), alkylthio (1–4C), primary amine (NH$_2$), alkyl (1–4C) secondary amine, dialkyl (1–4C) tertiary amino, dialkyl (1–4C) tertiary amine where the two alkyls are linked together to produce a morpholino, pyrrolidino or piperidino, acyloxy (1–4C), acylamido (1–4C) and thio analogs thereof, acetylaminoalkyl (1–4C), carboxy, alkoxycarbonyl (1–4C), carbamyl, alkylcarbamyl (1–4C), alkylsulfonyl (1–4C) or alkylphosphonyl (1–4C), wherein the hydrocarbyl can optionally be interrupted by a single ether (—O—) linkage; or wherein Y$^1$ and Y$^2$ are independently either morpholino, pyrrolidino, piperidino, NH$_2$, NHR', NR'R'O(CO)R', NH(CO)R', O(SO)R', or O(POR')R' in which R' is a hydrocarbyl (1–4C) which may be substituted with OH, NH$_2$, alkyl (1–4C) secondary amino, dialkyl (1–4C) tertiary amine, morpholino, pyrrolidino, piperidino, alkoxy (1–4C), or halogen substituents, or pharmacologically acceptable salt of said compound; and (b) administering to said mammal, from about one half hour to about twenty-four hours after administering said compound, an effective amount of carboplatin wherein a synergistic effect is derived from the administration of said compound and said carboplatin.

2. The method of claim 1 wherein said carboplatin is administered from about one hour to about eighteen hours after administering said compound.

3. The method of claim 2 wherein said carboplatin is administered from about two to about three hours after administering said compound.

4. The method of claim 1 wherein n is 1 and Y$^1$ and Y$^2$ are independently H or hydrocarbyl.

5. The method of claim 1 wherein said compound is 3-amino-1,2,4-benzotriazine 1,4-dioxide.

6. The method of claim 5 wherein said 3-amino-1,2,4-benzotriazine 1,4-dioxide is administered to said mammal in amounts of from about thirty milligrams to about seventy milligrams per kilogram body weight of said mammal.

7. The method of claim 1 wherein said compound is 3-amino-1,2,4-benzotriazine 1,4-dioxide and said chemotherapy agent is carboplatin.

8. A method of increasing the cytotoxicity of carboplatin towards a solid tumor, said tumor susceptible to treatment with said carboplatin, comprising administering to a mammal having such a tumor, from about one hour to about two hours after administering said carboplatin or from about one half hour to about twenty-four hours prior to administering said carboplatin, a cytotoxicity-enhancing amount of a compound having the formula

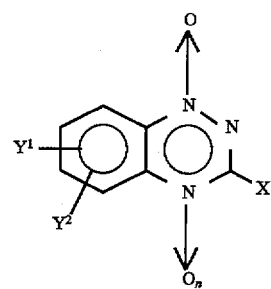

wherein X is NH$_2$;

n is 0 or 1; and

Y$^1$ and Y$^2$ are independently either H; nitro; halogen; hydrocarbyl (1–14C) including cyclic and unsaturated hydrocarbyl, optionally substituted with 1 or 2 substituents selected from the group consisting of halogen, hydroxy, epoxy, alkoxy (1–4C), alkylthio (1–4C), primary amino (NH$_2$), alkyl (1–4C) secondary amino, dialkyl (1–4C) tertiary amino, dialkyl (1–4C) tertiary amino where the two alkyls are linked together to produce a morpholino, pyrrolidino or piperidino, acyloxy (1–4C), acylamido (1–4C) and thio analogs thereof, acetylaminoalkyl (1–4C), carboxy, alkoxycarbonyl (1–4C), carbamyl, alkylcarbamyl (1–4C), alkylsulfonyl (1–4C) or alkylphosphonyl (1–4C), wherein the hydrocarbyl can optionally be interrupted by a single ether (—O—) linkage; or wherein Y$^1$ and Y$^2$ are independently either morpholino, pyrrolidino, piperidino, NH$_2$, NHR', NR'R'O(CO)R', NH(CO)R', O(SO)R', or O(POR')R' in which R' is a hydrocarbyl (1–4C) which may be substituted with OH, NH$_2$, alkyl (1–4C) secondary amino, dialkyl (1–4C) tertiary amino, morpholino, pyrrolidino, piperidino, alkoxy (1–4C), or halogen substituents, or pharmacologically acceptable salt of said compound wherein a synergistic effect is derived from the administration of said carboplatin and said compound.

9. The method of claim 8 wherein said compound is 3-amino-1,2,4-benzotriazine 1,4-dioxide.

10. The method of claim 8 wherein n is 1 and Y$^1$ and Y$^2$ are independently H or hydrocarbyl.

11. The method of claim 8 wherein said compound is administered from about one hour to about eighteen hours prior to administration of said carboplatin.

12. The method of claim 11 wherein said compound is administered from about 2 hours to about 5 and one half hours prior to administration of said carboplatin.

\* \* \* \* \*